United States Patent
Kim et al.

(10) Patent No.: US 6,566,525 B1
(45) Date of Patent: May 20, 2003

(54) PREPARATION OF N-SUBSTITUTED-HYDROXYCYCLOALKYLAMINE DERIVATIVES

(75) Inventors: Seong Jin Kim, Daejeon (KR); Keon Il Kim, Daejeon (KR); Kyoung Youl Yang, Daejeon (KR)

(73) Assignee: Samsung Fine Chemicals Co., Ltd., Ulsan (KR)

( * ) Notice: Subject to any disclaimer, the term of this patent is extended or adjusted under 35 U.S.C. 154(b) by 0 days.

(21) Appl. No.: 09/787,202

(22) PCT Filed: Sep. 15, 1999

(86) PCT No.: PCT/KR99/00553
§ 371 (c)(1),
(2), (4) Date: May 17, 2001

(87) PCT Pub. No.: WO00/15610
PCT Pub. Date: Mar. 23, 2000

(30) Foreign Application Priority Data

Sep. 17, 1998 (KR) .............................. 98-38476

(51) Int. Cl.$^7$ ............................................. C07D 211/42
(52) U.S. Cl. .................. 546/216; 548/541; 549/34; 549/40; 546/280.7
(58) Field of Search .............................. 546/216, 280.7; 548/541; 549/34, 40

(56) References Cited

U.S. PATENT DOCUMENTS

| | | | |
|---|---|---|---|
| 4,705,853 A | 11/1987 | Cale, Jr. | 540/490 |
| 4,916,141 A | 4/1990 | Sanchez | 514/300 |
| 4,937,235 A | 6/1990 | Trybulski et al. | 514/63 |
| 5,109,008 A | 4/1992 | Scopes et al. | 514/302 |
| 5,144,042 A | 9/1992 | Seido et al. | 548/541 |
| 5,233,053 A | 8/1993 | Cross et al. | 548/568 |
| 5,281,711 A | 1/1994 | Scherschlicht et al. | 546/95 |
| 5,364,872 A | 11/1994 | Tamazawa et al. | 514/343 |
| 5,463,064 A | 10/1995 | Tamazawa et al. | 506/281 |

OTHER PUBLICATIONS

Hercouet et al. "First asymmetric synthesis of . . . " Tetrhedron Assym. v. 7(5) 1267–1268 (1996).*
Chemfinder, carbon tetrachloride:physical properties (2002).*

* cited by examiner

Primary Examiner—Ceila Chang
(74) Attorney, Agent, or Firm—Lowe Hauptman Gilman & Berner, LLP

(57) ABSTRACT

A process for the preparation of N-substituted-hydroxycycloalkylamine derivatives, that are useful intermediates for the synthesis of various organic chemicals including pharmaceutical and agrochemical compounds, represented by formula (1), by reacting a 1,2-dihydroxalkyl alcohol, represented by the following formula (2), with a thionyl halide to produce an intermediate 1,2-cyclosulfinylalkyl halide represented by the following formula (3); and then cyclizing that intermediate with an amine compounds represented by the following formula (4).

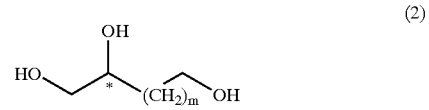

(2)

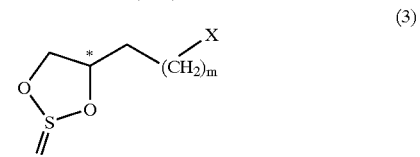

(3)

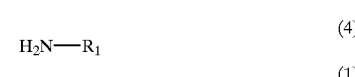

(4)

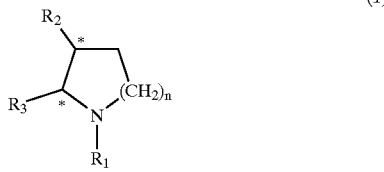

(1)

In the above structural formuli, * represents an asymmetric carbon atom; $R_1$ is hydrogen or an amino-protecting group; m is an integer of 1–3; and X is halogen. The reactant compounds as well as the compounds made according to this invention have the following substitution pattern:

n=1, $R_2$=OH, $R_3$=H and m=1; n=1, $R_2$=H, $R_3$=CH$_2$OH and m=2;

n=2, $R_2$=OH, $R_3$=H; and m=2; and n=2, $R_2$=H, $R_3$=CH$_2$OH and m=3.

8 Claims, No Drawings

PREPARATION OF N-SUBSTITUTED-HYDROXYCYCLOALKYLAMINE DERIVATIVES

This application is a 371 of PCT/KR99/00553 filed Sep. 15, 1999.

BACKGROUND OF THE INVENTION

Field of the Invention

The present invention relates to a process for a preparation of N-substituted-hydroxycycloalkylamine derivatives and more particularly, to the process for the preparation of N-substituted-hydroxycycloalkylamine derivatives represented in the following formula (1), regioselectively in high yield via 1,2-cyclosulfinylalkyl halide as an intermediate from the 1,2-dihydroxyalkyl alcohol as a starting material. Moreover, the synthetic method in this invention effectively provides optically active N-substituted-hydroxycycloalkylamine derivatives in high purity with regioselectivity and stereoselectivity, as well as racemic compounds, when optically active 1,2-dihydroxyalkyl alcohol is used as a starting material.

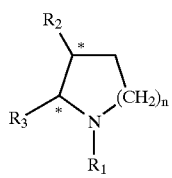

(1)

wherein,

* represents an asymmetric carbon;

$R_1$ is hydrogen or typical amino-protecting groups such as linear alkyl, branched alkyl, or cycloalkyl containing 1~10 carbon atoms or aromatic hydrocarbons;

$R_2$ is hydrogen or hydroxyl group;

$R_3$ is hydrogen or hydroxymethyl group; and n is 1 or 2.

N-substituted-hydroxycycloalkylamine derivatives are widely used as the intermediates for the synthesis of various organic compounds as well as pharmaceutical and agrochemical compounds. Especially, the optically active (R)- or (S)-N-substituted-3-hydroxypyrrolidine is generally known as the key intermediate in the preparation of pharmaceutical and agrochemical compounds. For example, the optically active N-substituted-3-hydroxypyrrolidine is used as the essential intermediate for the preparation of various pharmaceuticals such as carbapenem antibiotic (Panipenem), vasodilatin (Barnidipine), or antihypertensive in developing (Darifenacine, Lirequilli Clinafloxacine) [EP No. 483,580, No. 330,469, No. 304,087; U.S. Pat. Nos. 5,463,064, 5,364, 872, 5,281,711, 5,109,008, 4,916,141; International Patent WO 91/09013].

Several methods for the preparation of optically active 3-hydroxypyrrolidine derivatives have been reported as introduced hereinafter.

One of the most general methods for the preparation of N-substituted-3-hydroxypyrrolidine is the reduction of N-benzyl-3-hydroxysuccinimide using the reducing agent, lithium aluminum hydride (LAH), which is prepared by the reaction of d- or l-malic acid and benzyl amine [Synthetic Communications, 1983, 13(13), 1171~1123; Synthetic Communications, 1985, 15(7), 587~598; U.S. Pat. Nos. 5,109,008, 4,705,853].

Another method for the synthesis of N-substituted-3-hydroxypyrrolidine is the decarboxylation of (2S, 4R)-(–)-4-hydroxy-2-pyrrolidine carboxylic acid [International Patent WO 91/09013, U.S. Pat. No. 5,233,053].

Another method is the preparation of (S)-3-hydroxypyrrolidine by reduction of (S)-3-hydroxypyrrolidine derivatives developed by Eugene J. Trybulsky [U.S. Pat. No. 4,937,235].

However, the above conventional methods are not adequate to be introduced to industrial process, because of the delicate synthetic process, low yield, and expensive raw materials and reagents.

The preparation of (S)-3-hydroxypyrrolidine with hydroxybutyronitrile compounds has been reported [EP No. 269,258]. This method is effective on the preparation of 3-hydroxypyrrolidine as a racemic mixture. However, it can be hardly applied to industrial process, because the optically active 3-hydroxybutyro-4-nitrile, a key intermediate in the synthetic process of optically pure 3-hydroxypyrrolidine, is not easily prepared.

Inou and coworkers reported the preparation of 3-hydroxypyrrolidine from 4-chloro-3-hydroxybutyronitrile [EP No. 347,818]. According to this method, 3-hydroxypyrrolidine is prepared from (R)-2-acetoxy-3-chloropropyltosylate which is obtained by enzyme-mediated stereoselective hydrolysis of racemic epichlorohydrine. But, it has many problems to be utilized in industry because of the multi-step procedures and low yield.

Besides, several biochemical methods have been reported [JP Pyung 5-227991, Pyung 6-141876]: For example, the preparation of optically active N-substituted-3-hydroxypyrrolidine by selective deacetylation of racemic 3-acetoxy-N-benzylpyrrolidine using Lipase PS [Bull. Chem. Soc. Jpn., 1996, 69, 207~215], and the preparation of optically active N-substituted-3-hydroxypyrrolidine by enzyme-mediated stereoselective hydrolysis of N-substituted-3-acyloxypyrrolidine [International Patent WO 95/03421]. However, the application of the aforesaid biochemical synthetic process to industry needs to improve the process for the recovery of enzyme and separation/purification of reaction mixtures.

Also, the preparation of N-substituted-3-hydroxypyrrolidine from 1,2,4-butanetriol or its derivatives is reported, as described hereinafter [Heterocycles, 1987, 26 (8), 2247~2265].

Initially, 1,4-dibromo-2-butanol is prepared by the reaction of 1,2,4-butanetriol with hydrogen bromide via selective bromination of only primary alcohol at the position of C1 and C4, then reacted with benzyl amine and cyclized to yield N-benzyl-3-hydroxypyrrolidine [J. Med. Pharm. Chem., 1959, 1, 76]. But, the aforesaid bromination is not controlled easily, with very low yield of 31% and use of expensive bromination reagents.

The optically active 3-hydroxypyrrolidine is prepared from the optically active 4-halo-3-hydroxybutanol [EP No. 452,143, U.S. Pat. No. 5,144,042]. According to this method, the reduction of the ester of (S)-4-chloro-3-hydroxybutylic acid with calcium borohydride provides (S)-4-chloro-1,3-butanediol, and the subsequent selective sulfonylation of the only primary alcohol using methanesulfonyl chloride followed by the reaction with benzyl amine gives (S)-N-benzyl-3-hydroxypyrrolidine. In this process, it can't be considered as an economical method because the selective sulfonylation of only primary alcohol is difficult to result in good yield.

Moreover, the method for the preparation of the optically active N-benzyl-3-hydroxypyrrolidine by optical resolution is reported [JP Pyung 9-263578, Pyung 5-336992]. But, this process may not be recommended to prepare optically active compounds in high purity at the viewpoint of economics and efficiency.

Besides, other methods have been reported [EP No. 431,521].

Even though there are various methods for the preparation of optically active N-substituted-3-hydroxypyrrolidine derivatives as described above, it has been urgent to develop the method for the efficient preparation of cycloamine derivatives via cyclization of alkyltriol with higher yield and purity than those in the conventional methods.

SUMMARY OF THE INVENTION

The inventors in this invention have investigated for a long time that an efficient synthetic method for N-substituted-hydroxycycloalkylamine derivatives from 1,2-dihydroxyalkyl alcohol and eventually realized that the three hydroxyl groups, of the starting material, 1,2-dihydroxyalkyl alcohol, should be distinguished each other from the reactivity in the nucleophilic substitution.

To fit this requirement, both of the hydroxyl groups at C1, C2 positions of 1,2-dihydroxyalkyl alcohol were converted to a cyclic sulfite group by the reaction of 1,2-dihydroxyalkyl alcohol with thionyl chloride. The subsequent conversion of terminal hydroxyl group to halide provided 1,2-cyclosulfinylalkyl halide of which the functional groups showed different reactivities. Eventually, N-substituted-hydroxycycloalkylamine derivatives were prepared by the cyclosubstitution of the aforesaid alkyl halide with nucleophile such as amine compounds. Especially, optically active N-substituted-hydroxycycloalkylamine could be prepared in high purity with regioselectivity and stereoselectivity, if the optically pure 1,2-dihydroxyalkyl alcohol was used as a starting material.

Therefore, the purpose of this invention is to provide the synthetic method of racemic or optically active N-substituted-hydroxycycloalkylamine, as the target product, in maximum yield as well as high purity simultaneously inhibiting the side-reaction, racemization or formation of isomers which are usual problems in the conventional methods.

DETAILED DESCRIPTION OF THE INVENTION

This invention relates to the method for the preparation of racemic or optically active N-substituted-hydroxycycloalkylamine derivatives and the salts thereof represented in the following formula (1), which is characterized by the cyclosubstitution of nucleophile selected from the amine compounds represented in the following formula 4 to the racemic or optically active intermediate, 1,2-cyclosulfinylalkyl halide, represented in the following formula 3, which is prepared by the reaction of thionyl halide and 1,2-dihydroxyalkyl alcohol represented in the following formula (2) as a starting material.

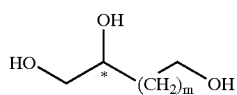

(2)

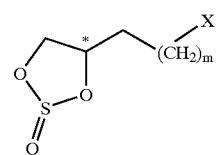

(3)

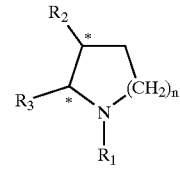

(4)

(1)

wherein, * represents an asymmetric carbon; X is halogen; $R_1$ is hydrogen, linear alkyl, branched alkyl, or cycloalkyl containing 1~10 carbon atoms or typical amino-protecting groups such as aromatic hydrocarbons; $R_2$ is hydrogen or hydroxyl group; $R_3$ is hydrogen, hydroxymethyl group; n is 1 or 2; m is an integer of 1~3.

The present invention is explained in more detail as set forth hereunder.

The present invention is composed of the following mechanisms: Among three hydroxyl groups of 1,2-dihydroxyalkyl alcohol, adjacent hydroxyl groups at 1- and 2-positions are activated by the conversion to cyclosulfinyl group which is a electrophilic protecting group. The terminal hydroxyl group is substituted with a halide providing more susceptible electrophilic site than the above cyclosulfinyl group, thus this halide is preferentially reacted with the nucleophilic amine to provide secondary amine, and then intramolecular cyclization occurs via the reaction of the amine with the electrophilic sulfinyl protecting group. The basic technique consisting of this invention is the intramolecular cyclization via nucleophilic substitution at the C1 or C2 position of the cyclic sulfinyl group with regioselectivity and stereoselectivity depending on the number of carbon in the secondary amine.

In the present invention, the intermediate represented in the aforesaid formula 3 is characteristically prepared by the sulfinylhalogenation in a specific condition using the thionyl halide, as a sulfinylhalogenation agent, which is relatively cheap and allows easy control of the reaction. Thus, the subsequent cyclization proceeds in high regioselectivity and stereoselectivity.

The synthetic method in this invention is applied to the preparation of racemic N-substituted-hydroxycycloalkylamine derivatives and salts thereof. Also, it can produce optically pure N-substituted-hydroxycycloalkylamine derivatives and salts thereof in high yield without racemization if optically active 1,2-dihydroxyalkyl alcohol shown in the aforesaid formula (2) is used as a starting material.

The procedure described in this invention for the preparation of racemic or optically active N-substituted-hydroxycycloalkylamine is briefly shown in the following reaction scheme 1.

Scheme 1

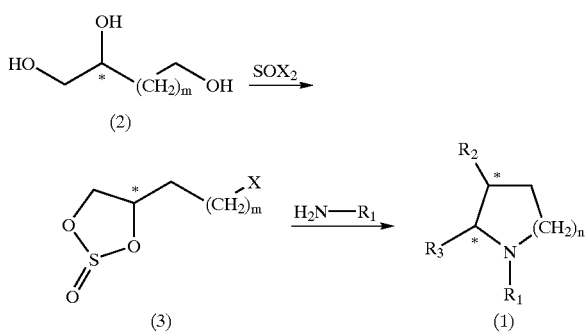

wherein, *, X, $R_1$, $R_2$, $R_3$, m, and n are respectively defined as the above-mentioned.

According to the above reaction scheme 1, the reaction of 1,2-dihydroxyalkyl alcohol represented in the above formula (2) with thionyl halide in the presence of base catalyst generates 1,2-cyclosulfinylalkyl halide represented in the above formula (3). To prepare the intermediate represented in the above formula (3) in higher yield and purity, the starting material represented in the above formula (2) is dissolved in aprotic polar solvent in the presence of base catalyst, then is slowly added thionyl halide at low temperature, desirable at −20° C.~10° C.

The halide is selected from F, Cl, Br, or I, more specifically Cl or Br is recommendable. Among the thionyl halide, thionyl chloride and thionyl bromide are commercially available. Thionyl chloride is recommended due to easy purchase in large scale and less heat generation during the reaction.

The amount of thionyl halide and base catalyst and the reaction temperature should be controlled to give high yield in the synthesis of the above intermediate. Of the excess amount of thionyl halide is used, then the large amount of by-products is formed, such as trihaloalkane due to the halogenation of all 1-, 2- and terminal hydroxyl groups. Thus, 2~4 (specifically 2~2.5) equivalents of thionyl halide is recommended to be used.

The solvent used in the present invention for the synthesis of intermediate includes aprotic organic solvents such as acetonitrile, methylene chloride, chloroform, carbon tetrachloride, and diethyl ether. Among them, acetonitrile, methylene chloride or chloroform is more desirable.

Either organic or inorganic salts can be used as a base catalyst even in excess amount. Both organic base such as triethylamine, tripropylamine, N,N-diisopropylamine, pyridine and the inorganic base such as potassium hydroxide, sodium carbonate, and potassium carbonate are desirable as base catalysts. Especially, it is recommended to use 2~3 equivalents of pyridine.

After the completion of the aforesaid reaction, the reaction mixture is filtrated to remove solids and added nonhydrophilic organic solvent, recommended methylene chloride or chloroform, then washed, in succession, with water and aqueous sodium hydrogen carbonate (a weak base) to remove remained acids. The evaporation of the solvent under reduced pressure provides pale yellowish liquid, which is then subjected to simple vacuum distillation to give racemic or optically active 1,2-cyclosulfinylalkyl halide as colorless liquid in high yield as well as purity, represented in the aforesaid formula (3).

The intermediate, 1,2-cyclosulfinylalkyl halide as shown in the above formula (3), is stable for a few months at the room temperature.

The racemic or optically active N-substituted-hydroxypyrrolidine derivatives represented in the above formula (1) is effectively prepared from the intermediate, 1,2-cyclosulfinylalkyl halide, represented in the formula (3) via the following procedures.

The racemic or optically active 1,2-cyclosulfinylalkyl halide represented in the above formula (3) is dissolved in aprotic polar solvent and cyclosubstituted by the reaction with amine in the presence of base catalyst. The cyclosubstitution is performed in the range of 0° C.~200° C., being recommended to reflux under the pressure ranged 1~10 atm depending on the amine. The organic solvent used in the cyclosubstitution includes a polar solvent such as acetonitrile, toluene, dimethylformamide, dimethylacetamide, dioxane, tetrahydrofuran, or pyridine. Among them, acetonitrile and dimethylacetamide are desirable. The basic catalysts include either organic base such as pyridine, triethylamine, diisopropylethylamine or the inorganic base such as sodium carbonate, potassium carbonate, calcium carbonate, sodium hydroxide, potassium hydroxide, sodium hydride, potassium hydride, calcium hydride, sodium methoxide, and sodium ethoxide. Among them, sodium carbonate and potassium carbonate are recommended.

The amine compounds participated in the cyclosustitution step as a reagent, are represented in the above formula (4). The more specific amine compound represented in the above formula (4) includes the alkylamines such as ammonia, methylamine, ethylamine, n-propylamine, iso-propylamine, n-butylamine, iso-butylamine, sec-butylamine, and the cycloalkylamine such cyclopropylamine, cyclobutylamine, cyclopentylamine, cyclohexylamine, and finally the aromatic amines such as phenylamine, benzylamine, methylbenzylamine, methoxybenzylamine, nitorbenzylamine, and optically active (S)- or (R)-methylbenzylamine. Besides, the typical amino protecting groups are included.

The desirable amount of the amine shown in the above formula (4) is in the range 1~10 equivalents for the efficient process.

For the efficient cyclosubstitution in this invention, a proper pressure and temperature were required. Consequently, the reaction was run for 2~48 hrs. The scheme 2 represents an example of the cyclosubstitution in this invention. The reaction of cyclosulfinylbutyl halide as represented in the above formula (3) with the benzylamine as represented in the above formula (4) for the cyclosubstitution gives N-benzyl-3-hydroxypyrrolidine as a main product without by-products such as an azidridine or azetidine compound.

Scheme 2

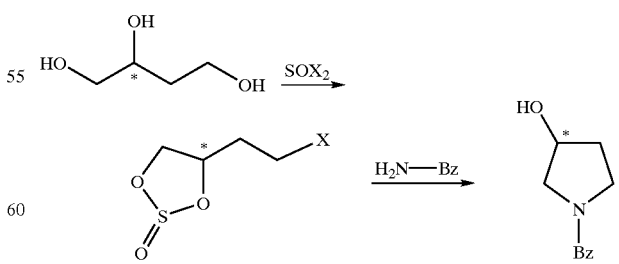

wherein, * represents an unsymmetrical carbon: X is halogen: $B_z$ is benzyl group.

The following scheme 3 represents another example of the cyclosubstitution in this invention. The reaction of the cyclosulfinylpentyl halide as shown in the aforesaid formula (3) with the benzylamine for the cyclosubstitution provides N-benzyl-3-hydroxypiperidine as the major product and the N-benzyl-2-hydroxymethylpyrrolidine as minor product.

Scheme 3

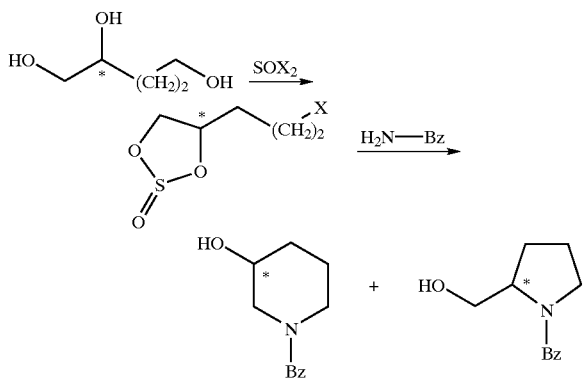

wherein, * represents an unsymmetrical carbon: X is halogen: $B_z$ is benzyl group.

The following scheme 4 represents another example of the cyclosubstitution in this invention. The reaction of the cyclosulfinylhexyl halide as shown in the aforesaid formula (3) with the benzylamine for the cyclosubstitution provides N-benzyl-2-hydroxymethyl-piperidine as the major product.

Scheme 4

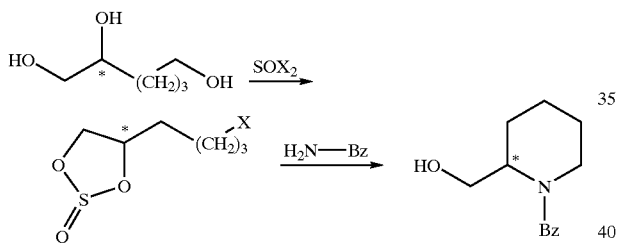

wherein, * represents an unsymmetrical carbon: X is halogen: $B_z$ is benzyl group.

The optically active N-substituted-hydroxycycloalkylamine derivatives are obtained from the cyclosubstitution using optically active cyclosulfinylalkyl halides as shown the above examples. The reaction of (S)-1,2-cyclosulfinyl-4-butylchloride or bromide with ammonia in high-pressure reactor for the cyclosubstitution also generated (S)-3-hydroxypyrrolidine in high yield.

Based on the aforesaid results, it is believed that the cycloalkylamine is formed by the nucleophilic substitution of amine (benzylamine) with the halide group in 1,2-cyclosulfinylalkyl halide followed by the intramolecular nucleophilic cyclization. Thermodynamically more stable cycloalkylamine is formed preferentially.

As described in this invention, the preparation of the cyclosulfinylalkyl halide, the intermediate for the cyclosubstitution as represented in the aforesaid formula (3), is advantageous over the conventional methods due to the short steps to run. With cyclosulfinylbutyl and cyclosulfinylhexyl halide, the optically pure and expensive (S)- or (R)-N-substituted-hydroxypyrrolidine and (S)- or (R)-N-substituted-hydroxymethylpiperidine derivatives, respectively, can be prepared in high yield and purity.

The synthetic methods described in this invention can provide the optically active (S)- or (R)-N-substituted-cycloalkylamine derivatives, without mentioning the racemate thereof, by using an optically active (S)- or (R)-1,2-hydroxyalkyl alcohol as a starting material. Besides, thionyl chloride used as a halogenating agent is economically advantage over the hydrogen bromide, since the thionyl chloride has the relatively low molecular weight compared to other protecting groups. Also, cyclosulfinyl group reacts and releases as sulfur dioxide upon the reaction progress, thereby enable the easy handling and separation of the gas by simple trapping resulting in small amount of waste.

Some of optically active 1,2-cyclosulfinylalkyl halides are reported in recent literatures as following.

Hercouet and coworkers used (S)-1,2-cyclosulfinyl-4-butyl chloride and 1,2-cyclosulfinyl-5-pentyl chloride as only an intermediate to prepare the cyclosulfate derivatives by simple oxidation in the synthesis of (−)-(2S, 3R)-methanepyrroline or (−)-(2S, 3R)-methanopipecolic acid [*Tetrahedron:* Asymmetry, 1996, 7(5), 1267~1268: *Tetrahedron Letters,* 1996, 37(26), 4529~4532]. Besides, the cyclosulfinyl groups are used as the simple protection group or the starting material for the preparation of the cyclic sulfate. But, it is not many cases for the purpose of nucleophilic substitution [*J. Am. Chem. Soc.,* 1998, 110, 7538~7539; *Tetrahedron:* Asymmnetry, 1996, 7(8), 2411~2416: *Synthesis,* 1992, 1035~1052; *Nucleic Acid Res.,* 1978, 5(3), 1029~1033: *Chem. Pharm. Bull.,* 1977, 2181; *Bull. Chem. Soc. Japan,* 1975, 48(11), 3243; *Chem. Rev.,* 1963, 63, 557~571].

The following specific examples are intended to be illustrative to the invention and should be construed as limiting the scope of the invention as defined by appended claims.

EXAMPLE 1

The Preparation of (S)-1,2-cyclosulfinyl-4-butyl chloride

Method A

To a solution of (S)-1,2,4-butanetriol (50.5 g, 0.47 mol) in acetonitrile (180 ml) was added pyridine (83.8 ml, 1.04 mol) with stirring, then cooled to 0° C. To this solution was slowly added thionyl chloride (75.4 ml, 1.03 mol) diluted with acetonitrile (70 ml) at a rate of not generating excess heat, then stirred for 2 at 0° C. hrs and then for additional 4 hrs at room temperature. The reaction was analyzed by using GC and TLC. After completion of the reaction, acetonitrile was removed under reduced pressure, and extracted with methylene chloride. The organic layer was washed, in succession, with water, 10% aqueous solution of sodium hydrogen carbonate, and water again, and then dried over sodium sulfate. The dried solution was filtrated and concentrated under reduced pressure, then distilled in vacuum to give 76.2 g of (S)-1,2-cyclosulfinyl-4-butyl chloride in 95.0% yield with 99.3% purity.

The product as a colorless transparent liquid was analyzed by NMR spectroscopy. The NMR spectrum of the product was identical with that of (S)-1,2-cyclosulfinyl-4-butyl chloride reported by Alain Hercouet [*Teratrahedron:* Asymmetry, 1996, 7(5), 1267~1268].

The ratio of isomers in the product was analyzed by GC [column: OV-101 (⅛"×10 ft), flow rate: 5.7 ml/min, injection temperature: 250° C., detector: FID, 280° C., column temperature: 170° C.]. The peaks of each isomer were observed at 6.22 min and 7.39 min with the ration of 1:1.7. The optical activity of the product was $[\alpha]_D=-7.47$ (c=1, MeOH).

Method B

To a solution of (S)-1,2,4-butanetriol (50 g, 0.47 mol) in methylene chloride (180 ml) was added pyridine (83.8 ml, 1.04 mol) with stirring, then the solution was cooled to 0° C. To this solution was slowly added thionyl chloride (75.4 ml, 1.03 mol) diluted with methylene chloride (70 ml) at a rate of not generating excess heat, then stirred for 2 hrs at 0° C. and for additional 4 hrs at room temperature. After completion of the reaction, it was extracted with methylene chloride. The separated organic layer was washed, in succession, with water, 10% aqueous sodium hydrogen carbonate solution, and water again, and then dried over sodium sulfate. The dried solution was filtrated and concentrated under reduced pressure, then distilled in vacuum to give 77.8 g of (S)-1,2-cyclosulfinyl-4-butyl chloride in 97% yield with the same analytical results as in the above method A.

EXAMPLE 2

The Preparation of (S)-1,2-cyclosulfinyl-4-butyl bromide

According to the similar procedure in the example 1, to a solution of (S)-1,2,4-butanetriol (50 g, 0.47 mol) in methylene chloride (180 ml) was added pyridine (83.8 ml, 1.04 mol) with stirring, then cooled to 0° C. To this solution was slowly added thionyl bromide (80.6 ml, 1.04 mol) diluted with methylene chloride (70 ml) at a rate of not generating excess heat, then stirred for 2 hrs at 0° C. and for additional 4 hrs at room temperature. After completion of the reaction, it was extracted with methylene chloride. The separated organic layer was washed, in succession, with water, 10% aqueous sodium hydrogencarbonate solution, and water again, and then dried over sodium sulfate. Dried methylene chloride solution was filtrated and distilled under reduced pressure to be concentrated. The concentrated reaction mixture was subjected to column chromatography on silica gel (15% ethyl acetate/hexane solution as an elute) to provide 93.5 g of (S)-1,2-cyclosulfinyl-4-butyl bromide in 93% yield with 98.6% purity.

The ration of each isomers of the product was 1:1.54 based on the peaks at 7.97, 8.84 min in GC under the same condition as shown in the example 1:

$^1$H-NMR (in CDCl$_3$, ppm): δ2.06~2.38 (1.6H, m), 2.47~2.60 (0.4H, m), 3.40~3.62 (2H, m), 4.08 (0.6H, dd), 4.44 (0.4H, t), 4.61 (0.4H, dd), 4.81 (1H, m), 5.20 (0.6H, m).

EXAMPLE 3

The Preparation of (S)-N-benzyl-3-hydroxypyrrolidine

Method A

To a solution of (S)-1,2-cyclosulfinyl-4-butyl chloride (10.0 g, 58.8 mmol) in acetonitrile (50 ml) in a round flask equipped with a reflux condenser was added potassium carbonate (24.4 g, 176.5 mmol) with stirring at room temperature and then added benzyl amine (19.3 ml, 176.8 mmol). The reaction mixture was heated at reflux for 12 hrs. After completion of the reaction, the reaction mixture was filtrated to remove solids and then the solvent was distilled off under reduced pressure. The residue obtained was purified by fractional distillation to provide 9.6 g of (S)-N-benzyl-3-hydroxypyrrolidine in 92% yield.

The NMR spectrum of the product was identical with that of (S)-N-benzyl-3-hydroxypyrrolidine purchased from Aldrich Co., or reported on the literature [U.S. Pat. No. 5,144, 042]. The optical purity of the product was 99.5% as same as that of the starting material, based on the liquid chromatographic analysis using Dicel O. D. column (hexane/isopropyl alcohol/diethyl amine=97:3:0.5, UV=254 nm, flow rate=1.0 ml/min) according to the known method [Japanese Patent Pyung 5-227991, Pyung 6-211782, Pyung 6-141876].

Method B

To a solution of (S)-1,2-cyclosulfinyl-4-butyl chloride (12.6 g, 58.9 mmol) in acetonitrile (50 ml) in a round flask equipped with a reflux condenser was added sodium carbonate (18.7 g, 176.4 mmol) with stirring at room temperature and then added benzyl amine (19.3 ml, 177 mmol). The reaction mixture was refluxed for 15 hrs. After completion of the reaction, the reaction mixture was filtrated to remove solids and then the solvent was distilled off under reduced pressure. The residue obtained was purified by fractional distillation to provide 9.8 g of (S)-N-benzyl-3-hydroxypyrrolidine in 94% yield. The analytic data of the product was identical with those in the above method A.

EXAMPLE 4

The Preparation of (S)-3-hydroxypyrrolidine

To a mixture of (S)-1,2-cyclosulfinyl-4-butyl chloride (5.0 g, 29.4 mmol) and sodium carbonate (9.35 g; 88.0 mmol) in acetonitrile (30 ml) in a high pressure reactor (500 ml) was introduced ammonia to maintain about 10 atm at 100~120° C. for 48 hrs. After completion of the reaction, the reaction mixture was filtrated and then concentrated to provide (S)-3-hydroxypyrrolidine with the unreacted starting material. The purification using column chromatography on silica gel (15%~50% ethyl acetate/hexane) gave 6.9 g of (S)-3-hydroxypyrrolidine in 90% yield, which was optically active and colorless. The NMR data of the product was identical with those in the known literature [EP No. 269,258, U.S. Pat. No. 5,233,053].

EXAMPLE 5

The Preparation of (S)-1,2-acetobutanol

To a solution of (S)-1,2,4-butanetriol (50 g, 0.47 mol) in acetone (250 ml) was added p-toluene sulfonic acid monohydrate (0.45 g, 2.3 mmol) at the room temperature with stirring for 12 hrs. After completion of reaction, acetone was removed off under reduced pressure. The residue obtained was subjected to the vacuum distillation to give 58.5 g of (S)-1,2-acetobutanol in 85% yield:

$^1$H-NMR (in CD$_3$OD, ppm): δ1.34 (3H, s), 1.39 (3H, s), 1.79 (2H, m), 3.56 (1H, t), 3.68 (2H, m), 4.08 (1H, dd), 4.22 (2H, qn).

EXAMPLE 6

The Preparation of (S)-1,2-aceto-4-metanesulfonyl butane (S)-1,2-acetobutanol (50 g, 0.342 mol) was dissolved in methylene chloride (250 ml) with stirring then cooled to 0° C. To this solution was added triethylamine (71.5 ml, 0.513 mol) and then methanesulfonyl chloride (31.8 ml, 0.41 mol) was added slowly at a rate of not generating excess heat, then stirred for 2 hrs at 0° C. and for additional 8 hrs at room temperature. After completion of the reaction, the solution formed was washed, in succession, with water, 50 ml of 0.1 N diluted hydrochloric acid, 10% sodium hydrogen carbonate solution, and then water again and dried over sodium sulfate. Dried methylene chloride solution was filtrated and evaporated under reduced pressure to be concentrated. The residue obtained was purified by column chromatography on silica gel to provide 54.9 g of (S)-1,2-aceto-4-methanesulfonyl butane in 71.6% yield:

$^1$H-NMR (in CDCl$_3$, ppm): δ1.35 (3H, s), 1.42 (3H, m), 2.00 (2H, m), 3.03 (3H, s), 3.61 (1H, t), 4.38 (2H, m).

EXAMPLE 7

The Preparation of (S)-1,2-aceto-4-cyanobutane

To a solution of (S)-1,2-aceto-4-methanesulfonyl butane (50 g, 0.223 mol) dissolved in acetonitrile (250 ml) in a round flask equipped with a reflux condenser was added potassium cyanide (43.6 g, 0.68 mmol) and refluxed for 15 hrs. After completion of the reaction, the solvent was removed off under reduced pressure. The residue thus formed was dissolved in water, extracted with ethyl acetate (300 ml) three times, and then, purified using column chromatography on silica gel to give 30.8 g of (S)-1,2-aceto-4-cyanobutane in 89% yield:

$^1$H-NMR (in CDCl$_3$, ppm): δ1.36 (3H, s), 1.42 (3H, s), 1.90 (2H, m), 2.53 (2H, m), 3.61 (1H, dd), 4.11 (1H, dd), 4.20 (1H, m).

EXAMPLE 8

The Preparation of (S)-1,2-aceto-4-pentanic acid sodium salt thereof

The solution of (S)-1,2-aceto-cyanobutane (20 g, 0.129 mol) in 20% aqueous sodium hydroxide solution (250 ml) was stirred at 90° C. for 8 hrs. After completion of the reaction, the solvent was removed off under reduced pressure. The residue thus formed was dissolved in methanol (100 ml), then neutralized using 50% sulfuric acid in methanol. The reaction mixture was filtrated to remove sodium sulfate, generated during neutralization, then methanol was removed off under reduced pressure to provide 20.73 g of (S)-1,2-aceto-4-pentanic acid sodium salt thereof in 82% yield:

$^1$H-NMR (in D$_2$O, ppm): δ1.18 (3H, s), 1.24 (3H, s), 1.63 (2H, m), 2.06 (2H, m), 3.44 (1H, t), 3.93 (1H, t), 4.02 (1H, qn).

EXAMPLE 9

The Preparation of (S)-1,2,5-pentanetriol (S)-1,2-aceto-4-pentanoic acid sodium salt thereof (20 g, 0.102 mol) was dissolved in tetrahydrofuran (200 ml) and the solution was cooled to 0° C. with stirring. Lithium aluminum hydride (19.4 g, 0.0.51 mmol) was added slowly at a rate not allowing the generation of excess heat. The mixture was stirred for 2 hrs at 0° C. and for additional 15 hrs at room temperature. At the end of the reaction, to the reaction mixture was added tetrahydrofuran (100 ml), then water (20 ml) slowly. In order to quench to remained lithium aluminum hydride, 15% aqueous sodium hydroxide solution (20 ml) and water (60 ml) were added, in sequence, then the precipitate was filtrated off. To the above reaction mixture, methanol (20 ml) and water (50 ml) were added, acidified to pH 1 with aqueous hydrogen chloride solution, and then stirred at room temperature for 3 hrs to hydrorize the protecting group, aceto-group. After neutralization using 10% solution of sodium hydroxide in methanol, the solvent was removed off under reduced pressure to provide 9.55 g of 1,2,5-pentanetriol in 78% yield:

$^1$H-NMR (in D$_3$O, ppm): δ1.13~1.65 (4H, m), 3.37 (1H, dd), 3.49 (3H, m), 3.60 (1H, m).

Optical purity: 99.1% (Gas Chromatographic analysis, B-TA capillary column).

EXAMPLE 10

The Preparation of (S)-1,2-cyclosulfinyl-5-pentyl chloride

To a solution of (S)-1,2,5-pentanetriol (10 g, 83.3 mmol, 99.5% purity) in methylene chloride (35 ml) was added pyridine (14.5 g, 183.3 ml), then cooled to 0° C. To this solution was added slowly thionyl chloride (13.4 ml, 183.7 mmol) diluted with methylene chloride (15 ml), stirred for 2 hrs at 0° C. and for 4 hrs at room temperature. The reaction mixture was washed with water, dried over sodium sulfate, filtrated, and concentrated under reduced pressure. The residue obtained was subjected to vacuum fractional distillation to provide 14.9 g of (S)-1,2-cyclosulfinyl-5-pentyl chloride in 97% yield with 99.5% purity.

The ratio of isomers in the product obtained was 1:1.29 (RT=11.1 and 11.56 min) based on the analysis data of GC [column: OV-101 (⅛"×10 ft), flow rate: 5.7 ml/min, injection temperature: 250° C., detector: FID, 280° C.]. [α]$_D$=−3.64, 25° C. (c=1, MeOH)

$^1$H-NMR (in CDCl$_3$, ppm): δ1.75~2.1 (4H, m), 3.61 (2H, m), 3.98 (0.5H, dd), 4.36 (0.5H, m), 4.53 (1H, m), 4.74 (0.5H, dd), 5.0 (0.5H, m).

EXAMPLE 11

The Preparation of (S)-1,2-cyclosulfinyl-5-pentyl bromide

To a solution of (S)-1,2,5-pentanetriol (10 g, 83.3 mmol) in methylene chloride (35 ml) was added pyridine (14.5 g, 183.3 ml), then cooled to 0° C. To this solution, thionyl bromide (14.2 ml, 183.3 mmol) diluted with methylene chloride (15 ml) was added slowly, stirred for 2 hrs at 0° C. and for 4 hrs at room temperature. The reaction mixture was washed with water, dried over sodium sulfate, filtrated, and concentrated under reduced pressure. The residue obtained was purified through column chromatography on silica gel, 15% ethyl acetate/hexane) to provide 17.5 g of (S)-1,2-cyclosulfinyl-5-pentyl bromide in 92% yield.

The ratio of isomers in the product obtained was 1:1.29 (RT=11.1 and 11.56 min) based on the analysic, data from GC [column: DB-1 (0.32 mm×30 m), flow rate: 1.2 ml/min, injection temperature: 250° C., detector: FID, 280° C., 70→290° C., 10° C/min].

$^1$H-NMR (in CDCl$_3$, ppm): δ1.75~2.2 (4H, m), 3.46 (2H, m), 3.97 (0.65H, dd), 4.34 (0.35H, m), 4.53 (0.7H, m), 4.71 (0.65H, dd), 4.99 (0.65H, dd).

EXAMPLE 12

The Preparation of (S)-N-benzyl-3-hydroxypiperridine

To a solution of (S)-1,2-cyclosulfinyl-5-pentyl chloride (10 g, 54.3 mmol) in acetonitrile (50 ml) in a round flask equipped with a reflux condenser were added sodium carbonate (17.3 g, 164.2 mmol) and benzylamine (17.5 g, 163.3 mmol). After being refluxed for 15 hrs to complete the reaction, the reaction mixture was filtrated to remove solids, then the solvent was evaporated under reduced pressure. The residue obtained was a mixture of (S)-N-benzyl-3-hydroxypiperridine and N-benzyl-2-hydroxymethylpyrrolidine in the ratio of 69.9%: 30.1% based on GC analysis [column: DB-1 (0.32 mm×30 m), flow rate: 1.2 ml/min, injection temperature: 250° C., detector: FID, 280° C., 70→290° C., 10° C./min]. The above mixture was purified by fractional vacuum distillation to give 8.1 g of (S)-benzyl-3-hydroxypiperridine in 75% yield. N-benzyl-2-hydroxymethylpyrrolidine, the by-product obtained, can be converted to 3-hydroxypiperridine according to the reported procedure [*Tetrahedron Letters*, 1995, 36(4), 549~522].

The NMR spectroscopic data of these compounds were identical with those shown in the literature (The Aldrich Library of NMR Spectra, Ed. II). The Optical purity was 98.9% based on the Mosher's method.

EXAMPLE 13

The Preparation of 1,2-cyclosulfinyl-6-hexyl chloride

The reaction mixture prepared with 1,2,5-hexanetriol (10 g, 74.6 mmol) as a starting material was purified by column chromatography on silica gel (15% ethyl acetate/hexane) to provide 14.0 g of 1,2-cyclosulfinyl-6-hexyl chloride in 95% yield, according to the similar procedure described in the example 10.

The ratio of isomers in the product obtained was 1:1.88 (RT=12.03 and 12.99 min) based on the GC data [column: OV-101 (1/8"×10 ft), flow rate: 5.7 ml/min, injection temperature: 250° C. detector: FID, 280° C., column temperature:170° C.].

$^1$H-NMR (in CDCl$_3$, ppm): δ1.5~2.1 (6H, m), 3.57 (2H, t), 3.97 (0.65H, t), 4.36 (0.35H, m), 4.53 (0.7H, m), 4.73 (0.65H, dd), 5.0 (0.65H, qn).

EXAMPLE 14

The Preparation of 1,2-cyclosulfinyl-6-hexyl bromide

According to the similar procedure as shown in the example 11 and 13, 1,2,6-hexanetriol (10 g, 74.6 mmol) and thionyl bromide (12.7 ml, 164.1 mmol) were added slowly to methylene chloride (15 ml). The reaction solution was stirred for 2 hrs at 0° C. and at for 4 hrs at room temperature to complete the reaction. The reaction mixture was washed with water, dried over sodium sulfate, filtrated, and then concentrated under reduced pressure. The purification using column chromatography on silica gel (15% ethyl acetate/hexane) gave 16.6 g of 1,2-cyclosulfinyl-6-hexyl bromide in 92% yield.

The ratio of isomers in the product obtained was 1:1.83 (RT=13.69 and 13.96 min) based on the analysic data from GC [column: DB-1 (0.32 mm×30 m), flow rate: 1.2 ml/min, injection temperature: 250° C., detector: FID, 280° C., 70→290° C., 10° C./min].

$^1$H-NMR (in CDCl$_3$, ppm): δ1.5–2.1 (6H, m), 3.44 (2H, t), 3.96 (0.65H, t), 4.36 (0.35H, m), 4.53 (0.7H, m), 4.72 (0.65H, dd), 5.00 (0.65H, qn).

EXAMPLE 15

The Preparation of (S)-N-benzyl-2-hydroxymethylpiperridine

To a solution of (S)-1,2-cyclosulfinyl-5-hexyl chloride (6 g, 30.3 mmol)) in acetonitrile (30 ml) in a round flask equipped with a reflux condenser were added sodium carbonate (9.64 g, 91.0. mmol) and benzylamine (9.75 g, 91.0 mmol), according to the similar procedure as shown in the example 12. After being refluxed for 15 hrs to complete the reaction, the reaction mixture was filtrated to remove solids and then the solvent was evaporated under reduced pressure. The purification of the product using column chromatography on silica gel gave 5.96 g of (S)-benzyl-3-hydroxymethylpiperridine in 96% yield. The expected by-product, 3-hydroxyazepine, was not formed at all.

$^1$H-NMR (in CDCl$_3$, ppm): δ1.5~1.75 (6H, m), 2.25 (1H, m), 2.6 (1H, m), 2.95 (1H, m), 3.48 (1H, d), 3.59 (1H, dd), 3.93 (1H, dd), 4.13 (1H, d), 7.28~7.37 (5H, m).

EXAMPLE 16

The Preparation of N-methyl-3-hydroxypyrrolidine

As shown in the example 4, To a mixture of (S)-1,2-cyclosulfinyl-4-butyl bromide (5.0 g, 23.3 mmol) and sodium carbonate (7.42 g, 70.0 mmol) in acetonitrile (30 ml) in a high pressure reactor (500 ml) was introduced excess methylamine to maintain about 10 atm for 36 hrs at 100~120° C. After completion of the reaction, the reaction mixture was filtrated and then concentrated to provide N-methyl-3-hydroxypyrrolidine with the unreacted starting material. The purification using the column chromatography on silica gel (15%~20% ethyl acetate/hexane) gave 2.0 g of colorless N-methyl-3-hydroxypyrrolidine in 85% yield. The NMR data of the product was identical with those in the known literature [EP No. 269,258].

As shown above, some major characteristics of the process according to this invention are followings:

it is simple and economical.

it has high stereoselectivity and regioselectivity in cyclization reaction because of using an intermediate, 1,2-cyclosulfinylalkyl halide which is very stable at room temperature.

it does not contain racemization at chiral center during the reaction.

it is very effective on the production of optically active N-substituted-hydroxycycloalkylamine and racemic compounds in industrial scale because of easy control of the reaction.

What is claimed is:

1. A process for the preparation of N-substituted-hydroxycycloalkylamine derivatives represented by formula (1), which process comprises:

(a) reacting; 1,2-dihydroxalkyl alcohol, represented by formula (2), with thionyl halide to produce an intermediate 1,2-cyclosulfinylalkyl halide represented by formula (3); and (b) cyclizing the intermediate 1,2-cyclosulfinylalkyl halide represented by formula (3) with at least one nucleophilic compound selected from the group consisting of the amine compounds represented by formula (4):

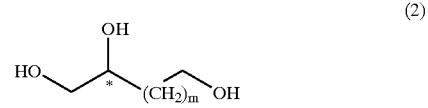

(2)

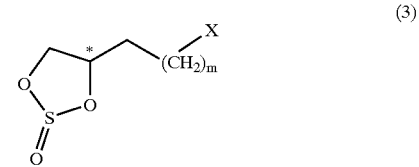

(3)

(4)

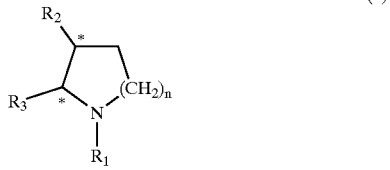

(1)

wherein:

* represents an asymmetric carbon atom;

R$_1$ is hydrogen or an amino-protecting group; and

X is halogen; and wherein said compound 1 is further selected from the group consisting of compounds in which:

where m=1, n=1, $R_2$=OH, and $R_3$=H;
where m=2, n=1, $R_2$=H, and $R_3$=CH$_2$OH;
where m=2, n=2, $R_2$=OH, and $R_3$=H; and
where m=3, n=2, $R_2$=H, and $R_3$=CH$_2$OH.

2. The process according to claim 1, wherein the compound of formula (1) is racemic or optically active.

3. The process according to claim 1, wherein said thionyl halide is thionyl bromide or thlonyl chloride.

4. The process according to claim 1, wherein the intermediate represented in the above formula (3) is produced by reacting 2.0~4.0 equivalents of thionyl halide with a basic catalyst in an aprotic polar solvent.

5. The process according to claim 4, wherein said aprotic polar solvent is acetonitrile or methylene chloride.

6. The process according to claim 4, wherein said basic catalyst is at least one member selected from the group consisting pyridine, triethylamine, tripropylamine, and N,N-diisopropylethylamine.

7. The process according to claim 1, wherein said cyclization is carried out at 0° C.~200° C., using 1.0~10.0 equivalents of the amine compound as the nucleophilic compound represented by formula (4).

8. The process according to claim 1, wherein the amine compound represented in the above formula (4) is selected from ammonia, methylamine, ethylamine, n-propylamine, i-propylamine, n-butylamine, i-butylamine, sec-butylamine, cyclopropylamine, cyclobutylamine, cyclopentylamine, cyclohexylamine, phenylamine, benzylamine, methylbenzylamine, methoxybenzylamine, nitrobenzylamine, and optically active (S)- or (R)-methylbenzylamine.

* * * * *